United States Patent [19]
Mirzabekov et al.

[11] Patent Number: 5,851,772
[45] Date of Patent: Dec. 22, 1998

[54] MICROCHIP METHOD FOR THE ENRICHMENT OF SPECIFIC DNA SEQUENCES

[75] Inventors: Andrei Darievich Mirzabekov; Yuri Petrovich Lysov, both of Moscow, Russian Federation; Valentine Vladimirovich Shick, Hinsdale, Ill.; Svetlana Alekseevna Dubiley, Moscow, Russian Federation

[73] Assignee: University of Chicago, Chicago, Ill.

[21] Appl. No.: 593,345

[22] Filed: Jan. 29, 1996

[51] Int. Cl.$^6$ ............................. C12Q 1/68; C07H 21/04

[52] U.S. Cl. ............................. 435/6; 536/24.3; 935/77; 935/78

[58] Field of Search ............................. 435/6; 536/24.3, 536/25.32; 935/77, 78

[56] References Cited

U.S. PATENT DOCUMENTS 5,434,049  7/1995  Okano et al. .................................. 435/6
5,552,278  9/1996  Brenner ......................................... 435/6

OTHER PUBLICATIONS

Saiki et al., Proc. Natl. Acad. Sci. 86:6230–6234, Aug. 1989.
Matthews et al., Analytical Biochemistry 169:1–25, Feb. 1988.

*Primary Examiner*—W. Gary Jones
*Assistant Examiner*—Debra Shoemaker
*Attorney, Agent, or Firm*—Cherskov & Flaynik

[57] ABSTRACT

A method for enriching specific genetic material sequences is provided, whereby oligonucleotide molecules complementary to the desired genetic material is first used to isolate the genetic material from a first source of genomic material. Then the genetic material is used as a label to isolate similar genetic sequences from other sources.

19 Claims, 4 Drawing Sheets

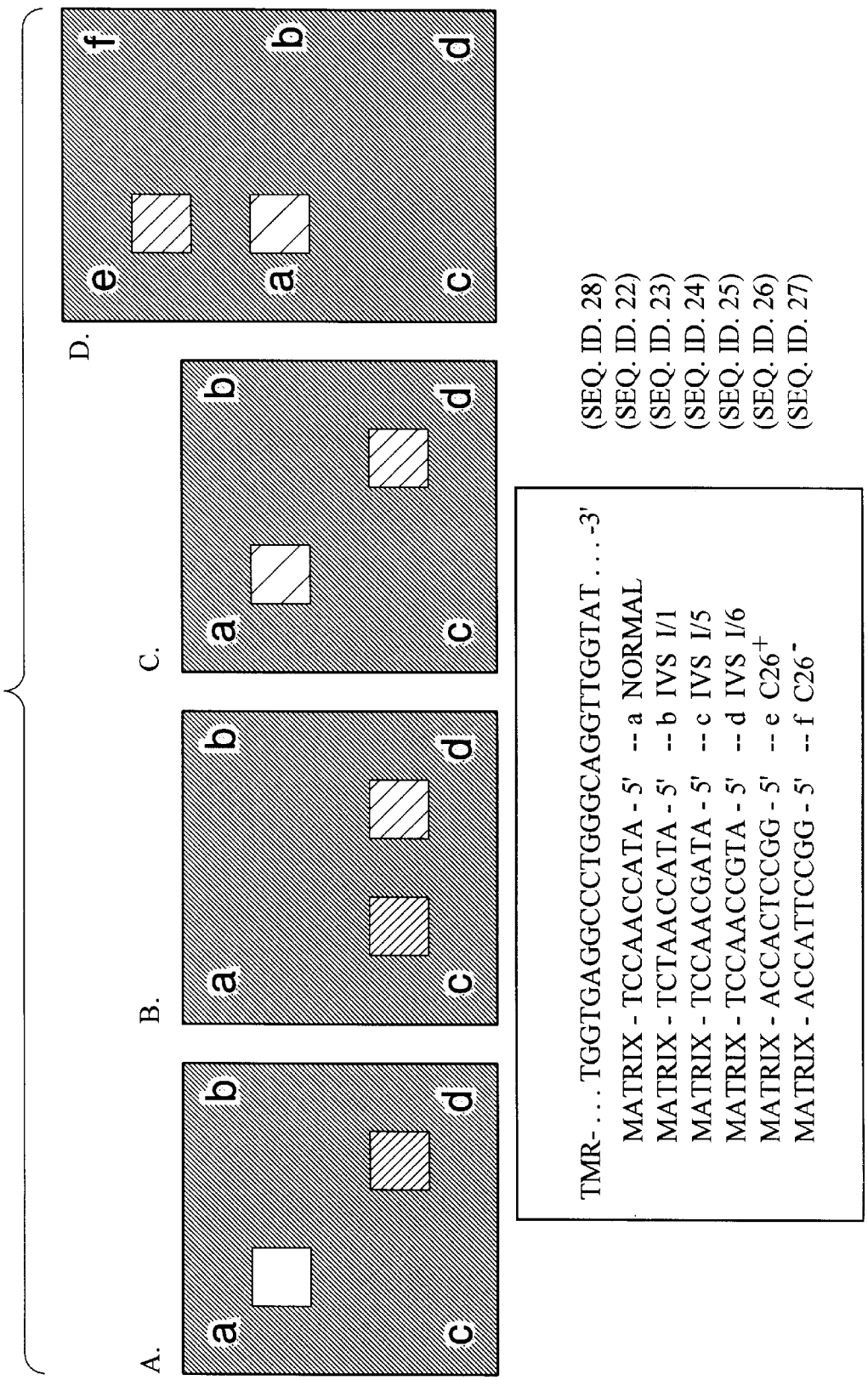

MICROCHIP METHOD FOR THE ENRICHMENT OF SPECIFIC DNA SEQUENCES

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to a method for harvesting specific DNA fragments, and more particularly this invention describes a method for using Sequencing by Hybridization to Oligonucleotide Microchips to isolate, identify and enrich specific DNA fragments.

2. Background of the Invention

The identification and harvesting of desired DNA sequences has tremendous potential. The isolation and subsequent proliferation of sequences coding for certain desired proteins is but one example.

Unfortunately, applying typical sequencing and mutation identification methods to harvesting efforts yield less than ideal results. Such efforts result in low product yield. One method, by P. R. Wallace et al., *Nucleic Acid Res.* 6, 3543–3557, involves attaching a test DNA molecule to a membrane and then performing hybridizations with labeled oligonucleotides. That technique is designed only to identify individual base substitutions, and is not capable of optimizing mutant or allele yields and related exons.

In addition to the various sequencing and mutation identification methods currently used, a number of methods of nucleic acid fractionation methods also are employed in efforts to enrich certain DNA fragments. For example, gel electrophoresis is used to separate DNA and RNA according to molecular size. Other approaches separate nucleic acids based on physico-chemical characteristics. These approaches include HPLC, fractionation according to thermal stability, and the presence of mismatches. Furthermore, hybridization properties and differences in hybridization kinetics have been exploited in a number of applications, for example to isolate mRNAs on poly dT columns, to fractionate sequences present in different copies, and to make subtractive DNA libraries.

The drawbacks to current methods for sequence enrichment procedures discussed above are numerous, however. Gel electrophoresis is a time consuming process that does not adapt well to clinical settings. And experienced laboratory personnel are required in HPLC processes to ensure that consistent, reproducible results are obtained. Furthermore, the simultaneous fractionation of many probes prior to identification are not facilitated by either of these methods.

An emerging sequencing strategy that has the potential for being adapted for use in enriching procedures deals with the use of oligonucleotide matrices. This sequencing technique strives to contact target DNA to thousands of oligonucleotides, which are first immobilized at fixed positions in a polyacrylamide gel. The high capacity gels used in this technique, popularly called sequencing by hybridization to oligonucleotide microchips (SHOM), make this method attractive for sequencing. Aside from the work of the inventors, however, SHOM is not yet perfected for sequencing, let alone enrichment of isolated fragments. A primary drawback of SHOM is the tendency for hairpin structures in long molecules of single-stranded DNA may result in duplexing.

Another drawback to SHOM is that the procedures for manufacturing sequencing microchips with the required, large number of immobilized oligonucleotides are not perfected. For example, if immobilized octamers are utilized to determine the positions of each of the four bases in genomic DNA, then $4^8$ or 65,536 such octamers need to be fabricated and subsequently immobilized in the gel. Conversely, if less than all iterations of an immobilized oligomer are to be utilized, no protocol currently exists for determining how many immobilized oligomers are needed to assure adequate screening for target sequences.

A need exists in the art to provide genetic material harvesting methods that are efficient and cost effective. The method should solve typical problems associated with sequencing by hybridization with oligonucleotide matrices, including minimizing intramolecular interactions of desired genetic material, minimizing the costs for preparing oligonucleotide matrices, and improving the discrimination of perfect duplexing from imperfect duplexing.

SUMMARY OF THE INVENTION

It is an object of the present invention to provide a method for enriching and identifying specific genetic material that overcomes many of the disadvantages of the prior art.

Another object of the present invention is to provide an efficient, accurate and high capacity method for enriching specific sequences of genetic material. A feature of the invention is the fragmentation of the genetic material prior to its hybridization. An advantage of the present invention is the more efficient and complete utilization of the porous characteristics of the gel matrices to increase the yields of desired sequences.

Yet another object of the present invention is to provide a method for isolating target DNA sequences and subsequently enriching the sequences. A feature of the present invention is the use of a two-step oligonucleotide matrix procedure. An advantage of the present invention is that the process is a highly accurate method for identifying and enriching target oligonucleotide sequences.

Still another object of the present invention to provide an easy method for identifying and subsequently enriching specific sequences of DNA. A feature of the present invention is the ease of use of a large number of oligomers immobilized on a fractionation chip and which are complementary to the desired DNA sequences, to isolate the target sequences contained on ss DNA. An advantage of the invented method is the dramatic reduction in the required number of immobilized oligomers to pinpoint desired DNA sequences compared to typical SHOM sequencing techniques. Another advantage of the invented method is the use of simple blotting or electrophoresis techniques to quickly transfer isolated fragments to sequencing gel-matrices for rapid enrichment of the isolated fragments.

Another object of the present invention is to provide a more accurate method for identifying and enriching specific sequences of DNA. A feature of the invented method is the incorporation of universal bases in the sequences of immobilized oligonucleotides contained on the sequencing polyacrylamide matrix. An advantage of the invention is the enhanced stability rendered to the resulting duplex, and the higher level of discrimination between perfect matching and non-perfect matching.

Briefly, the above and other objects and advantages of the invention are achieved by providing a method for isolating and enriching a plurality specific genetic material sequences comprising immobilizing oligonucleotide molecules of a predetermined length on a predetermined position on a first substrate, said oligonucleotide molecules synthesized to complement base sequences of the plurality of specific genetic material sequences; contacting the specific genetic material with said immobilized oligonucleotides to allow formation of duplexes between said oligonucleotides and each of the specific genetic material sequences; isolating each of the specific genetic material sequences from the duplexes formed; labeling each of the now-isolated specific genetic material with a fluorochrome; contacting each of the now labeled genetic material with a second substrate, whereby said second substrate contains a plurality of groups of immobilized oligonucleotides, each group complementary to a sub-sequence region of each of the now labeled genetic material, so as to allow for duplexes to form between the now labeled genetic material and said specific sub-sequences and thereby identify the now labeled genetic material.

BRIEF DESCRIPTION OF THE DRAWING

The present invention together with the above and other objects and advantages may best be understood from the following detailed description of the embodiment of the invention illustrated in the drawings, wherein:

FIG. 4 is a schematic depiction of the duplex formed between gel-immobilized decamers and subject DNA, in accordance with the present invention.

DETAILED DESCRIPTION OF THE INVENTION

A method for isolating, identifying, and enhancing specific oligonucleotide sequences has been developed. The present invention exploits the high porosity and the facilitation of high oligonucleotide densities of polyacrylamide gels to produce a plurality of oligonucleotide matrices to first isolate target sequences and then identify the isolated sequences. As more completely disclosed infra, the invented procedure is suitable for use as an enrichment tool for certain nucleic acid sequences.

An initial procedure involves the manufacture of the oligonucleotide matrices or microchips. The microchips contain a selection of immobilized synthetic oligomers, said oligomers synthesized so as to contain complementary sequences for desired portions of DNA. The oligomers are then hybridized with cloned or polymerase chain reaction (PCR) amplified nucleic acids comprising the desired mutated region, said hybridization occurring under stringent conditions, outlined infra. The high stringency conditions insure that only perfect or near perfect matches between the sequence embedded in the microchip and the target sequence will occur during hybridization.

After each initial hybridization, the chip is washed to remove most mismatched fragments. The reaction mixture is then denatured to remove the bound DNA fragments, which are subsequently labeled with a fluorescent marker.

A second round of hybridization with the labeled DNA fragments is then carried out on sequence microchips containing a different set of immobilized oligonucleotides. These fragments first may be cleaved into smaller lengths. The different set of immobilized nucleotides may contain oligonucleotides needed for whole sequencing, partial sequencing, sequencing comparison, or sequence identification. Ultimately, the fluorescence from this second hybridization step can be detected by an epifluorescence microscope coupled to a CCD camera.

The invented enrichment technique, with its unique two-step application of SHOM, increases the efficiency for the simultaneous isolation of many fragments by at least 10 fold, and more typically, by factors of 100.

Fractionation Detail

Figure 1:
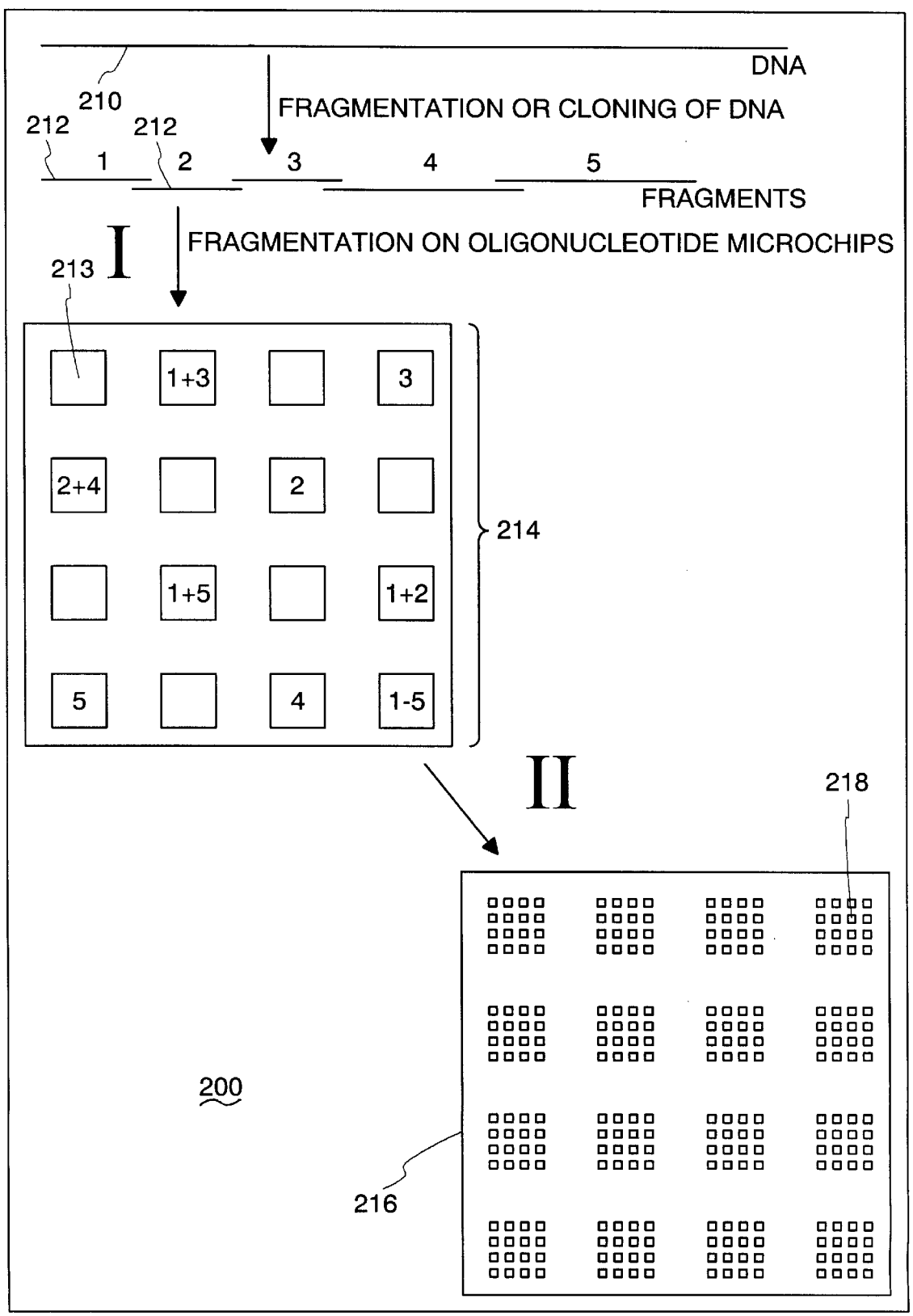
FIG. 1 is a schematic depiction of an exemplary two step fractionation sequencing procedure, in accordance with the present invention.

The invented fractionation procedure is depicted in FIG. 1 as numeral 200. As shown in FIG. 1, long strands of nucleic acids 210 are fragmented into short pieces 212. These short pieces 212 are hybridized with complementary oligonucleotide sequences which are immobilized in individual gel cells 213, all of which comprise a fractionation matrix 214. After the fragments are isolated from each other, the now-isolated fragments are labeled and then transferred from the fractionation microchip 214 to an array of microchips 216 so as to enrich and identify the isolated fragments. Each element 218 of the enriching microchip 216 may itself be an array of gel cells, with each cell therein loaded with a predetermined and particular oligonucleotide complementary to a target sequence found on the wild oligonucleotide strand 210. Identification of the sequence is determined by observing the fluorescence emanating from those cells wherein duplexing between the labeled fragment 212 and the predetermined immobilized nucleotide occurs.

The sizes of the fractionation chip 214 and the sequencing chip 218 can be similar, with their arrays similarly arranged. In this way, it is possible to directly transfer DNA fractions from the fractionation chip 214 to the corresponding number of cells in the sequencing chip 218. This can be done through blotting. If the fractionation chip 214 is kept above the melting temperature of its duplexes, and the sequencing chip 218 is kept below that temperature, the hybridized fragments will naturally diffuse from the former to the later matrix, thereby vastly simplifying DNA transfer procedures. Electrophoresis techniques also can be used for DNA transfer from one microchip to another.

In as much as not all cells of the fractionation matrix will capture fragments, one-to-one cell relationships between matrices often is excessive. A more economical way of to array sequence cells is for the cells to correspond to the topology of those fractionated matrix elements that contain fractionated DNA. In as much as the DNA to be initially fractionated is also fluorescently labeled, the resulting fluorescence emanating from the fractionation chip after duplexing is detected by standard optical detection techniques.

Fractionation Chip Size Detail

The inventors have found that when choosing the proper size of the fractionation chip 214, a balance between fractionation efficiency and chip size is a factor. Chips having all possible 15-mers ($4^{15}$=1,073,741,824) or 20-mers ($4^{20}$=1,099,511,627,776) would allow for fractionation of all the fragments of a bacterial or mammalian genome. However, simpler tasks will require simpler chips with fewer immobilized elements. If the sequence of DNA to be fractionated is known, then only those oligonucleotides complementary to the target sequences need be fabricated and immobilized.

Figure 2:
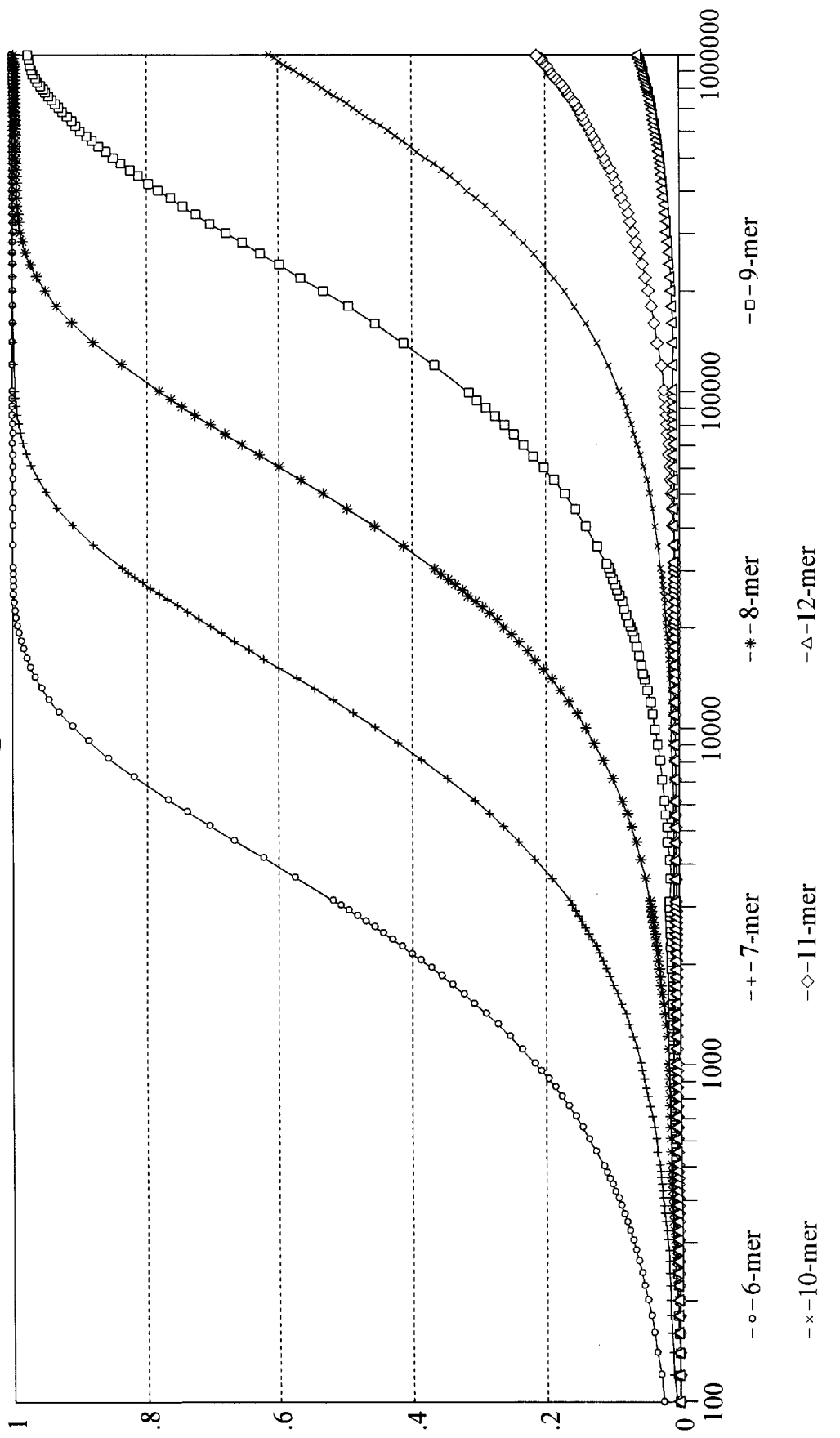
FIG. 2 is graphical representation of probabilities of oligonucleotide presence in genetic fragments, in accordance with the present invention.

Certain events occur relatively infrequently but at a regular rate. The probability of such an event occurring is given by the Poisson distribution. If the DNA sequence is unknown, then probability calculations, resulting in FIG. 2, must be utilized. FIG. 2 illustrates that the shorter the immobilized oligonucleotide, relative to the DNA fragment, the higher the probability that the complementary oligonucleotide sequence is present in the sequence. FIG. 2 shows the probabilities $P_0$ of the presence of an oligomer, having a length m ranging from six to 12 bases, in random fragments which range in size from 100 to 1 million bases long.

While the use of shorter oligonucleotides increases the probability of its hybridization with a longer fragment, the use of shorter oligomers also increases the likelihood of its appearance on several different fragments. Therefore, another parameter, $N_{0.5}$, is utilized to determine the efficiency of the fractionation chip. $N_{0.5}$ is defined as the maximal number of different fragments that can be fractionated on oligonucleotides of a certain length when not less than half of the occupied cells 213 in the matrix 214 contain only one fragment. The inventors have found that if a higher number of fragments than $N_{0.5}$, is sought to be isolated, many cells 213 of the matrix 214 will contain a mixture of fragments, leading to inefficient fractionation results.

To increase the desired result of fragment separation, every fragment should be isolated in at least two cells. This will restrict the number of fragments, which need to be separated by oligonucleotide matrices containing K number of nucleotides, to $N_{2,K}$. As such, $N_{2,K}$ depends on the number of cells 213 on the fractionization matrix 214 while $N_{0.5}$ does not.

In determining optimal fractionation matrix 214 parameters, one also must consider the probability M that every DNA will be isolated by hybridization with a fractionation chip 214 containing K oligonucleotide cells. M increases with the increase of K.

Tables 1–3 shows the values for P, K, $N_{0.5}$, and $N_{2,M\%}$ ($N_{2,M\%}=N_{2,K}$ when K equals the minimal number of oligonucleotides that provide M% probability for the fractionation of every fragment) for fractionation matrices containing oligonucleotides of different sizes when applied to fractionation of fragments of different lengths.

TABLE 1

Fractionation Chip Parameters When 256 bp length DNA Fragments Are Produced

| $L_{olig}$ | $N_{0.5}$ | $K_{95\%}$ | $N_{2,90\%}$ | $K_{95\%}$ | $N_{2,95\%}$ | $K_{99\%}$ | $N_{2,99\%}$ | $K_{99.9\%}$ | $N_{2,99.9\%}$ |
|---|---|---|---|---|---|---|---|---|---|
| 6 | 13 | 37 | 3 | 48 | 7 | 74 | 11 | 111 | 14 |
| 7 | 48 | 148 | 10 | 192 | 24 | 295 | 41 | 443 | 53 |
| 8 | >1,000 | 590 | 36 | 767 | 91 | 1179 | 160 | 1769 | 599 |

Table 1 above provides data for fragments that average 256 base pairs in length. This is because the restriction endonucleases, which are used to produce the fragments and which are specific to four base sequences, typically produce 256 bp long sequences. Plasmid DNA approximately 5,000 bp typically generate approximately 20 fragments of 256 bp lengths. Taking into account the statistical calculations disclosed in Table 1, most efficient fractionation of this DNA would be with a chip having approximately 300 immobilized 7-mers. Table 1 calculations also show that cosmid DNA having a length of about 30,000 bp would generate about 120 fragments, each approximately 250 bases long, that can be separated on a chip with approximately 1,000 to 1,500 8-mers.

TABLE 2

Fractionation Chip Parameters When 4096 bp length DNA Fragments Are Produced

| $L_{olig}$ | $N_{0.5}$ | $K_{90\%}$ | $N_{2,90\%}$ | $K_{95\%}$ | $N_{2,95\%}$ | $K_{99\%}$ | $N_{2,99\%}$ | $K_{99.9\%}$ | $N_{2,99.9\%}$ |
|---|---|---|---|---|---|---|---|---|---|
| 7 | 5 | 10 | 2 | 12 | 3 | 19 | 4 | 28 | 5 |
| 8 | 13 | 37 | 3 | 48 | 7 | 74 | 11 | 111 | 14 |
| 9 | 48 | 148 | 10 | 192 | 24 | 295 | 41 | 443 | 53 |
| 10 | >1000 | 590 | 36 | 767 | 91 | 1179 | 160 | 1769 | 599 |

Approximately 4,000 base long fragments are generated by restriction endonucleases specific to 6 base pairs (average length 4096). Cosmids (30,000 bp), BAC (100,000 bp) and YAC (500,000 bp), produce approximately 7, 25, and 120 fragments respectively when contacted with these endonucleases. Table 2 shows that chips containing 30–50 octamers could be used for fractionating cosmid fragments. Chips containing 150–300 9-mers can be used for bacterial autosomal chromosome (BAC) fractionation and 1000 10-mers can be used for efficient fractionation of yeast autosomal chromosome (YAC).

TABLE 3

Fractionation Chip Parameters When 32768 bp length DNA Fragments Are Produced

| $L_{olig}$ | $N_{0.5}$ | $K_{90\%}$ | $N_{2,90\%}$ | $K_{95\%}$ | $N_{2,95\%}$ | $K_{99\%}$ | $N_{2,99\%}$ | $K_{99.9\%}$ | $N_{2,99.9\%}$ |
|---|---|---|---|---|---|---|---|---|---|
| 9 | 8 | 19 | 2 | 24 | 4 | 37 | 6 | 56 | 8 |
| 10 | 25 | 74 | 19 | 96 | 13 | 148 | 21 | 222 | 27 |
| 11 | 93 | 295 | 18 | 384 | 46 | 590 | 81 | 885 | 104 |

The inventors have found that there are several practical obstacles to consider when fabricating fractionation chips. One of these is molecule size. Generally, an increase in porosity of the gel will accommodate larger molecule sizes. Polyamide or other organic gels such as agarose gel, and inorganic substrates such as Sol-Gel (or other silicate glass matrices), as well as porous glass, will accommodate large molecules.

Another obstacle in the fractionation, sequencing, and sequence identification of DNA procedures is the formation of hairpin structures. Hairpin formation is avoided when molecules are identified. To decrease the interference of hairpin structures at the hybridization interface, modifications to the immobilized oligomer can be made. For example, modifications to the base structures can result in more stable duplexes. These modifications include the substitution of adenine by diaminopurine, and thymidine by bromedeoxyuridine. Also, substitutions of the phosphodiester groups by peptide, methylphosphonate or guanidino groups will make the resulting heteroduplexes between oligonucleotides and DNA more stable than homoduplexes, and provide efficient competition of intra-strand and inter-strand duplex formation.

Another obstacle is that during hybridization, several duplexes containing mismatches are formed in parallel with perfect duplexes within the same cell. This decreases fractionation efficiency. Such mismatched duplexes should be washed off the cell, while the perfectly matched DNA remains. The inventors have found that shorter nucleotides (8-mers to 12-mers) provide higher discrimination data between perfect and mismatched duplexes.

Typical methods of fragmentation are used, including partial depurinization/depyrimidization effected by formic acid/hydrazine treatment, and splitting of these sites by amines, piperidine, and hydroxyl radicals degradation. Generally, long strands of nucleic acids, prior to contact with the sequencing chip 216, are fragmented into short pieces (10–50 nucleotides). Then, these short, fragmented pieces, lacking hairpins, are allowed to permeate into the oligonucleotide-containing gel cells 218 on the sequencing matrix 216 to hybridize with those oligonucleotides containing complementary sequences.

Microchip Detail

Suitable immobilization substrates must have high capacity, be relatively rigid and durable, and should be benign viz hybridization. The use of gel-support for oligonucleotide immobilization offers many additional advantages. Oligonucleotides are tethered into the gel volume instead of being attached to the surface. The gel capacity for immobilization is between approximately 300 and 30,000 femto moles (1 fm=$10^{-15}$ moles) which is many magnitudes higher than the capacity of glass. Therefore, each gel cell is treated as a test tube containing immobilized nucleotides and separated from each other by a hydrophobic glass surface. As noted earlier, a myriad of different matrix materials or carriers can be used to serve as immobilizing substrates, including, but not limited to, polyacrylamide gel, other polyamide gels, agarose and silicate glass matrices, such as Sol-Gel. The capacity of a potential carrier can be initially evaluated by immobilizing the same amount of fluorochrome-labeled oligonucleotide diluted by unlabeled oligonucleotide to various intensities. When dealing with polyacrylamide, 100 pmoles of a cold oligonucleotide per one cell (i.e., per 1 mm of surface area or 0.03 $m^3$ of gel volume), is a suitable loading goal. Similar experiments with an oxidized periodate labeled with [$^{\alpha 32}P$] UTP have shown that the gel capacity is equal to about 1 nmole per 1 $mm^2$ of the gel surface, which corresponds to a 30 mM concentration of active groups on the gel. An exemplary gel thickness is 20 microns ($\mu$m). The concentration of amide groups, some of which are first converted to hydrazide groups to facilitate oligo attachment as discussed infra, is 1M in 8 percent polyacrylamide.

The porous structure of the gel also facilitates more thorough hybridization and subsequent washing, mismatch discrimination, and a more efficient use of DNA fractionation techniques, disclosed infra.

A matrix of polyacrylamide gel-elements is prepared by first polymerizing a 10–30 $\mu$m gel-layer on a glass surface. A myriad of techniques are available, including that disclosed by K. R. Khrapko et al. *J. DNA Sequencing and Mapping* Vol 1, pp. 375–388, and incorporated herein by reference.

Strips of gel are then removed in perpendicular directions to yield gel squares. Each square is isolated from adjacent squares by strips of naked glass, said strips wide enough to prevent accidental mixing of oligomers. The inventors have found that widths of between approximately 80 $\mu$m and 200 $\mu$m provide good results. A scribing machine facilitates this removal, but photolithography methods are also applicable for the preparation of such gel-square elements. A laser method, developed by the inventors and disclosed in PCT/RU 92/00052, 1992 to Yershov, and incorporated herein by reference, is also suitable.

Gel-element sizes range from approximately 25 $\mu$m×25 $\mu$m×20 $\mu$m for a micro-chip to 1 mm×1 mm×30 $\mu$m for macro-chips. Generally, chip sizes ranging from 20 $\mu$m×20 $\mu$m×20 $\mu$m to 1 mm×1 mm×30 $\mu$m produce good results. In as much as polyacrylamide gels have low fluorescent background, the sensitivity of the measurements (i.e., the ratio of signal to background) will increase with miniaturization of the gel-cell sizes, resulting in an increase in density of the DNA-oligonucleotide duplexes. The inventors were able to detect fluorescence down to 10 amol of labeled target per 100 $\mu$m×100 $\mu$m. Microchip gel-elements fixed on a glass plate can be a myriad of sizes. A chip of 1 cm×1 cm may contain tens of thousands of elements as small as 25×25×20 $\mu$m.

Oligonucleotide Synthesis Detail

The synthesis of oligonucleotides for immobilization starts from 3-methyluridine, located at the 3'-end, as described in Krapko, noted supra. Oligonucleotides for hybridization are labeled with TMR at the 3'-end by terminal transferase, provided by Promega (Madison, Wis.), and fluorescently labeled dUTP. Alternatively, the 5' amino-group is labeled with an excess of N-hydroxysuccinimide ester of 5-carboxytetramethylrhodamine (Molecular Probe, Inc. Eugene, Oreg.) in DMSO with 50 mM sodium borate buffer, pH 9.0 at 60° C. for 30 minutes. The labeled oligonucleotides are further purified by polyacrylamide gel electrophoresis (PAGE) and recovered as described in J. L. Mergny et al. *Nucleic Acid. Res.* 22, 920–928.

The synthesis of oligonucleotides containing universal bases is similar.

Oligonucleotides containing the 3-methyluridine at the 3' end are effective couplers through the aldehyde groups formed after oxidation of the 3-terminal ribose residues with sodium periodate. Prior to transfer to the gel, up to 2 nmole of oligonucleotide solution is initially oxidized in 1 mM to 10 mM $NalO_4$ at room temperature for approximately 10 minutes. Oligonucleotides are lyophilized, dissolved in water, and then used for spotting, or alternatively, stored in the wells, 2 mm in diameter, of the teflon microliter plate, where the oxidation was initially carried out. Attachment occurs between the oxidized 3' terminal residue of the oligo and the hydrazide groups of partially modified polyacrylamide gel, whereby the gel was first activated by converting some amide moieties to hydrazide ones.

The 3-methyluridine is a good anchor in as much as it forms no stable base pairs with subject DNA.

Oligonucleotide is applied by robot onto the gel-elements in aliquots of 1 nanoliter ($10^{-9}$ liter) or more. The application technique uses a thin thermostabilised metal pin with a hydrophobic side surface and a hydrophilic end-face which determines the spotting volume. Pin temperature is kept close to the dew point to avoid evaporation of the water solution containing the oligonucleotides. This transfer technique, developed by the applicants, is more fully disclosed in PCT No. 94 000189, by Yershov, and incorporated herein by reference.

Once the micro-volumes of the solutions of the bioorganic compounds (the oligomers) have been applied to all cells of the matrix, the micro-matrix temperature is set equal to or below the dew point of the ambient air. The temperature is maintained until swelling of the gel is complete and non-coalescent droplets of water condensate appear in the spacings between the cells. Then, a thin layer of an inert non-luminescent oil (such as NUJOR Mineral Oil from Plough, Inc.) is applied to the micro-matrix surface, the thickness of the layer being over approximately 100 $\mu$m. The micromatrix is kept under the oil layer until the immobilization process is complete, preferably for at least 48 hours. The oil is then removed with a solvent, such as ethanol and water, and the matrix is dried and stored ready-for-use. More detailed discussion of the foregoing matrix preparation procedure is found in PCT 94 00178, and incorporated herein by reference.

The bond between an oligonucleotide and polyacrylamide is stable enough for the matrix to withstand 10–15 rounds of hybridization without any noticeable degradation. The half-life of the oligonucleotide-gel bond at 60° C. is 2 hours, and at 25° C., 36 hours.

Oligonucleotides are immobilized on the gel in spaced arrays so as to prevent interference during hybridization and also to enhance hybridization efficiencies. Gel-loading capacity limits of between 0.01 percent and 30 percent yield good results, with a preferable range of between approximately 0.1 percent and 10 percent. Concentrations of the oligo to the subject DNA can vary, and generally range from between 100 to 1,000 times higher in concentration compared to the subject DNA. Convenient subject DNA concentrations range from 0.1 to 1 picomole (pmole=$10^{-12}$ moles) in one microliter, and a typical oligo concentration is 100 fmoles (fmole=$10^{-15}$ moles) per gel element of 100 square centimeters.

The inventors observed that more than 70 percent of gel-immobilized oligonucleotides formed duplexes with DNA. The effective temperature stability of duplexes formed between DNA and gel-immobilized oligonucleotides depend on their concentrations and base-pair lengths. Generally, the inventors obtain good DNA complexing with immobilized oligomers at temperatures ranging from between approximately 0° C. and 60° C. Duplexing is further enhanced at high temperatures when oligonucleotides with relatively long base-pair lengths (e.g. 10-mers and 12-mers) are used. For example, when using immobilized pentamers, good duplexing occurs at between 0° C. and 10° C. When using immobilized octamers, preferable temperatures are selected from a range of between approximately 25° C. to 45° C. across the 0.01 percent to 30 percent gel capacity spectrum. This flexibility in gel loading provides the ability to equalize the stability of AT- and GC-rich duplexes during hybridization.

Hybridization. Washing and Staining Detail

To maintain gels at specific dew temperatures, all procedures are performed on a Peltie thermotable or similar temperature regulating device. Hybridization of a microchip with fluorescently labeled DNA is carried out at 0° C. for 30 minutes in 1–10 $\mu$l of washing buffer with 1 percent TWEEN 20 (Calbiochem, La Jolla, Calif.) detergent or any other detergent, specifically a detergent containing polyoxyethylenes. Washing buffer contained 1M NaCl, 5 mM Na phosphate (pH 7.0), 1 mM EDTA. Thereafter 100 $\mu$l of washing buffer was pipetted on the microchip at 0° C. for 10 seconds and carefully pipetted off to remove unhybridized DNA. The washing could be repeated by varying the temperature and duration.

Fluorescence Analysis Detail

A multi-wave length fluorescence microscope coupled with a CCD-camera was assembled for image analysis. An objective yielding a 3-mm observation field enabled the simultaneous analysis of over 1,000 elements of the microchip at once. Specifically, the microscope (350 W high pressure mercury lamp, Ploem opaque with interference excitation and barrier filters for TMR) equipped with special optics and a CCD camera was built. The $3^\times$ objective with the 0.4 numerical aperture allows the illumination of the object field up to 7 mm in diameter and project 2.7×2.7 mm of the microchip on the CCD matrix. The CCD head is similar to that manufactured by Princeton Instruments (Trenton, N.J.). The exposure time varied from 0.4 to 30 seconds with a readout time of about 1.3 seconds. Variation in the sensitivity within the object area did not exceed 5 percent. The system allows operation with $1.7^\times$ objective with the same numerical aperture for analyzing 5×5 microchip areas. The instant configuration allows for rapid change-out of Filters for different fluorochromes.

The image of the microchip on the CCD camera was accommodated by a microcomputer, similar to the configuration disclosed in Khrapko, K. R. et al. *J. DNA Sequencing and Mapping*, 1, pp. 375–388, and incorporated herein by reference. For printing, linear transformation was used. This brought the highest pixel values to the same level for all images. For digital estimation, the image of the microchip element was fully covered by a 'square' twice the size of the element. Then a frame was constructed around the 'square' with equal square area. The signal of the element was calculated as the signal from the square minus the signal from the frame.

Fluorochrome Detail

Tetramethylrodamine (TMR) was used as a dye for labeling the genetic materials. Other dyes that are suitable labeling compounds include, but are not limited to, fluoresceine, Texas Red, Cascade Blue, and rhodamine, all available from Molecular Probes. HEX™, marketed by Applied Biosystems in Foster City, Calif., is another suitable dye. In the case of DNA-labeling, before measurements the microchip is incubated with fluorescent tagged DNA at 0° C. for 30 minutes and then rinsed for 10 seconds with washing buffer to remove unbound targets. Perfect duplexes are discriminated already in the process of hybridization despite rather high intensities of the fluorescence signal from the unbound target.

More effective discrimination of perfect duplexes from mismatched ones are achieved by plotting the dissociation curve either at temperature gradient or at a fixed temperature while changing the duration of washing. Real-time measurements allowed for the choice of optimal conditions for discrimination when the mismatched signals are close to background levels. Temperatures are controlled by a Peltie thermotable.

PCR Detail

PCR amplifications were performed by an adapted procedure by Postnikov et al. *Hemoglobin* 17,439–453 (1993), and incorporated herein by reference. Initially, amplification of 421 bp-long product was carried out with 1 ng of genomic DNA, primers #12005 TGCCAGAAGAGCCAAGGA-CAGG (SEQ. ID. 1) and #12406 TAAGGGTGG-GAAAATAGACC (SEQ. ID. 2). The reaction conditions were as follows: 30 cycles with 40 seconds at 93° C., 30 seconds at 67° C. and 30 seconds at 72° C. 5 $\mu$l of the PCR were transferred to the reaction mixture for amplification with nested primers. Nested primers, #12156 CATTTGCT-TCTGACACAACT (SEQ. ID. 3) and #12313 TCTCCT-TAAACCTGTCTTG (SEQ. ID. 4), were used to amplify 176 bp-long DNA for 25 cycles (30 seconds at 90° C., 30 seconds at 50° C., 20 seconds at 72° C.). The PCR with fluorescently nested primers (labeled #12272 CCCTGGGCAG (SEQ. ID. 5) and normal #12299 GTCT-TGTAACCTTG (SEQ. ID. 6)) was carried out for 25 cycles (30 seconds at 80° C., 30 seconds at 35° C.) and yielded 32 bp product. PCR was purified by PAGE or by enrichment procedures.

EXAMPLE 1

Figure 3:
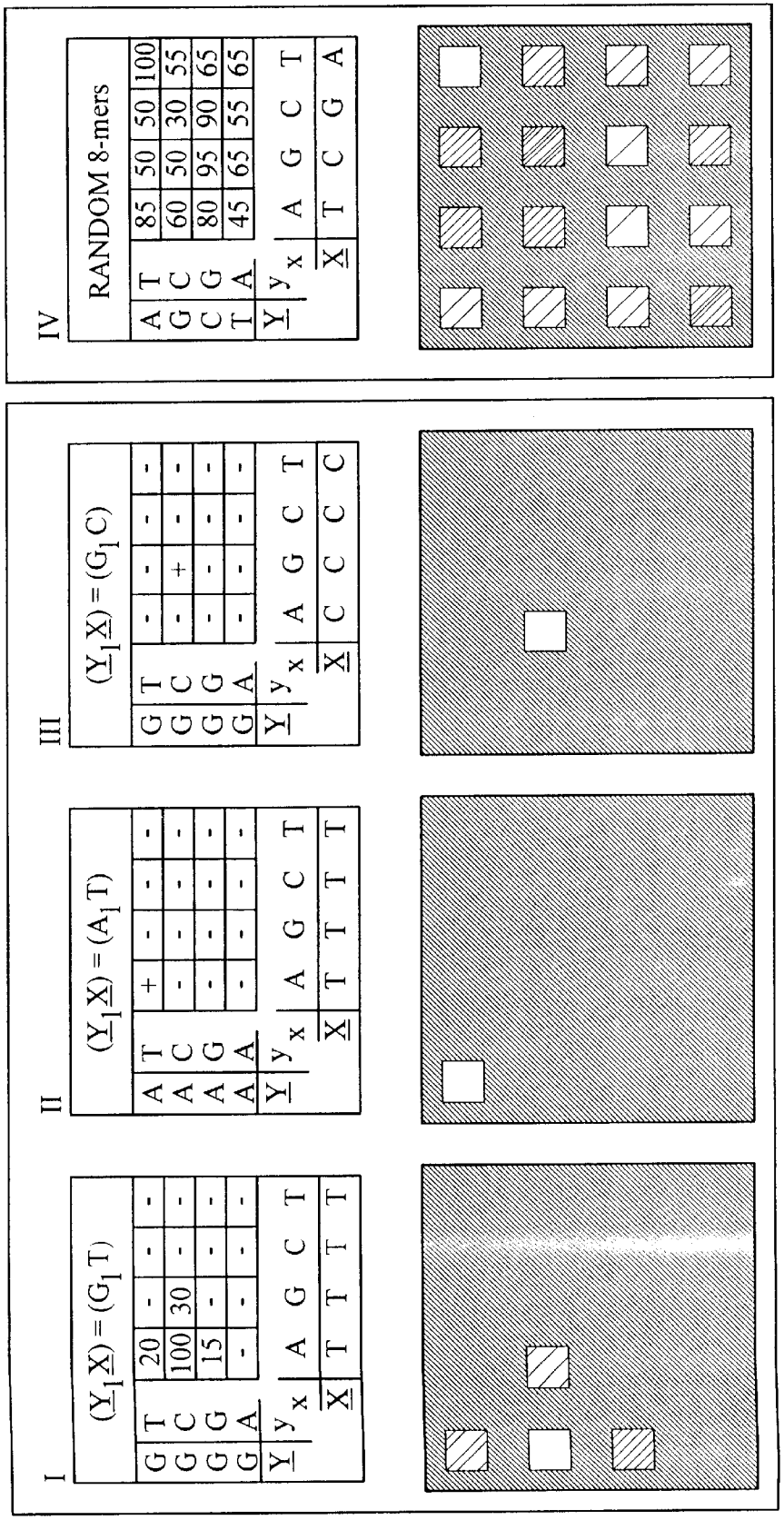
FIG. 3 is a schematic depiction of the duplex formed between gel-immobilized octamers and target DNA, in accordance with the present invention.

Well-studied β-thalassemia mutations, IVS I in the first intron of the β-globin gene, were chosen for the sequence analysis. A set of 16 octamers was synthesized and immobilized on a matrix, as is shown in FIG. 3. These oligonucleotides can identify any base changes in positions IVS I/1 and IVS I/6. The microchip was successively hybridized with three TMR-labeled 19 mers corresponding to a normal allele, IVS I/1 (G→A)and IVS I/6 (C→T) mutations. All base changes were identified immediately after hybridization: the signals from perfect duplexes were observed as bright fluorescent spots. Single mismatches and double mismatches gave, respectively, weak signals or no signals at all.

Washing of the microchip for another 5 minutes at 20° C. in washing buffer enhanced the difference between the perfect and single-mismatched duplexes: for the most stable penultimate $^5$'TG$^3$' (X=T, x=G) mismatch (FIG. 3, I-A) from 3 to 10 times. The quantitative intensities of the microchip elements were normalized to the intensity obtained when the microchip was hybridized with the degenerated fluorescently labeled 8-mers (FIG. 3, IV-A). The hybridization with degenerated 8-mer also confirmed the good quality of matrix preparation: all 16 spots showed similar fluorescence intensities.

The hybridization pattern itself provides sufficient information about perfect duplexes. FIG. 3 shows that strong signals from perfect duplexes ("+") are localized on intersections of horizontal and vertical lines ('cross pattern') corresponding to the signals for single-mismatched duplexes ("−"). Even if discrimination of perfect duplexes from mismatched ones is not achieved, the analysis of the cross pattern can reveal the perfect duplexes. A double cross pattern was observed upon hybridizing the mixture of two 19-mers with a microchip, which corresponds to heterozygote mutations.

As noted, supra, the invented method facilitates the isolation and identification of target DNA sequences which are first fractionated. In one procedure, DNA was fragmented by chemical reactions used in the purine/pyrimidine modification method, as outlined in Maxam, A. M. et al. *Proc. Natl. Acad. Sci. U.S.A.* 74,560–564, and incorporated herein by reference. The precipitated PCR products (up to 10 $\mu$g) were dissolved in 90 percent formic acid and incubated at room temperature for 10 minutes, then precipitated with 10 volumes of acetone with 2 percent $LiCLO_4$ and washed twice with acetone. Pellets were dissolved in 80 percent hydrazine, incubated at room temperature for 30 minutes, and precipitated with 30 volumes of acetone. The cleavage of modified residues was performed 1M piperidine at 95° C. for 30 minutes followed by chloroform extraction and precipitation. The resulting products were dephosphorylated using a CIAP Kit (Promega), extracted with phenol/chloroform, precipitated with acetone and dissolved in 2 $\mu$l of 0.1× wash buffer. An enriching chip was prepared by immobilizing an oligonucleotide mixture (5–10 pmol each) on a 1×1 mm gel element. The chip was hybridized with fragmented DNA at 20° C. for 1 hour and washed at 0° C., 15° C. and 20° C. for 10 minutes at each step with 30 ml of 0.1× wash buffer. The hybridized fragments were eluted from the gel by three washings for 5 minutes with 25 $\mu$l of 1M $LiClO_4$ in 50 percent formamide at 30° C. The solutions were pooled and the DNA was precipitated with 1 ml of acetone with 2 percent $LiClO_4$.

Six decamers, shown in FIG. 4 as "a" (SEQ. ID. 22), "b" (SEQ ID. 23), "c" (SEQ. ID. 24), "d" (SEQ. ID. 25), "e" (SEQ. ID. 26), and "f" (SEQ. ID. 27), were immobilized on a 1×1 mm gel-element of a macro-matrix. Fragmented PCR product (SEQ. ID. 28) comprising the region was hybridized with the macrochip under the high stringency conditions noted above where only duplexes with high stability (mainly perfect duplexes) are formed. After denaturation, the bound fragments were recovered, fluorescently labeled and used for hybridization with a microchip. Fragmentation processes, combined with high gel capacities, lead to a 20-fold enrichment for DNA fragments complementary to immobilized decamers, with more than an 80 percent recovery yield.

EXAMPLE 2

DNA from the blood of β-thalassemia patients was used for diagnosis of various mutations within the first intron of β-globin gene. At first, DNA was amplified by using primers to obtain a 421 bp fragment. Then the nested primers were used to synthesize a 176 bp fragment or fluorescently labeled 32 bp fragment.

The 176 bp DNA was chopped by the purine/pyrimidine modification method and enriched on a macrochip as described supra. Fluorescently labeled enriched fragments of 176 bp product or 32 bp long PCR were hybridized with a diagnostic microchip containing immobilized decamers. Decanucleotides were chosen because of their higher efficiency in hybridization as compared with octamers; an observation that is further exploited by the inventors and disclosed infra whereby universal bases are incorporated into the sequences of immobilized oligos.

No essential difference was observed upon hybridization of 32 bp or fragmented 176 bp PCR DNA.

Analysis of over 30 samples of DNA showed that DNA from different sources bearing the same mutations have the same hybridization pattern; i.e., the cross-ratios of the hybridization signals for different microchip elements remained nearly constant, as can be noted in a/d in FIG. 4C. Mutation images provide useful information for recognition of particular mutations or duplexes, thereby serving as a vehicle to identify desired DNA sequences for subsequent enrichment.

EXAMPLE 3
DNA Fractionation

Three oligonucleotides (10 pmoles each) were separately immobilized on a three gel element fraction chip, with dimensions of 1×1×0.2 mm. The oligonucleotides were complementary to three subfragments of the b-globin gene. Three PCR fluorescently labeled fragments were synthesized simultaneously in one tube on a plasmid that contains the three exons of the b-globin gene with the following mixture of primers: 5'-CACTTAGACCTCACCCTAGTG-3' (SEQ. ID. 7), 5'-GACTTTTATGCCCAGCCCTG-3' (SEQ. ID. 8), 5'-GAGAAGTCTGCCGTTACTGC-3' (SEQ. ID. 9), 5'ACCTTGATACCAACCTGCCC-3' (SEQ. ID. 10), 5'-GTGGAGACAGAGAAGACTCTT-3' (SEQ. ID. 11), and 5'-TAGACCATAGGCAGAGAGAG-3' (SEQ. ID. 12). The PCR fragments were hybridized with the fractionation chip. The DNA was eluted from each chip element and hybridized with a sequencing microchip. The microchip contained the following nine octamers: 5'-GATTGGCC-3' (SEQ. ID. 13), 5'-CTGGGAGT-3' (SEQ. ID. 14), 5'-TCCCTGCT-3' (SEQ. ID. 15), 5'-TTGCCCCA-3' (SEQ. ID. 16), 5'-CGTTCACC-3' (SEQ. ID. 17), 5'-CCACCACT-3' (SEQ. ID. 18), 5'-CCCAAGAG-3' (SEQ. ID. 19), 5'-CCTATCAG-3' (SEQ. ID. 20), and 5'-GTCAGTGC-3' (SEQ. ID. 21). These octamers are complementary to the PCR fragments (three octamers for every subfragment). The fractionation procedure separated all three PCR fragments from each other and the subsequent hybridization with the sequencing microchip demonstrated the efficiency of the fractionation and identified the fragments.

EXAMPLE 4
RNA Fractionation

Three RNA transcripts were synthesized on the plasmids containing T7 RNA polymerase promoters. The transcripts contained the regions of three subfragments of the b-globin gene. The transcripts were first hybridized with the fractionation chip. RNA was eluted from each cell of the chip and then hybridized with the sequencing microchip used in example 3. The procedure proved as efficient as that for DNA fractionation.

Universal Base Detail

Another method for minimizing hairpin formation of lengthy DNA molecules, aside from the fractionation procedure outlined supra, is the use of universal bases (e.g. 5-nitroindole, 3-nitropyrrole, and inosine in immobilized oligonucleotide fractions. Attaching said universal bases on the 5', and/or the 3' end of the gel-attached oligo, depending of course on which end is tethered to the gel, increases oligo length. The inventor has found that increased length results in higher stability of the duplexes between the target DNA and the immobilized oligos. As such, duplex formation prevails over hairpin formation.

The incorporation of universal bases also allows for the transfer of terminal mismatches into internal ones, thereby resulting in better discrimination between perfect duplexes and mismatched ones.

While the invention has been described with reference to details of the illustrated embodiment, these details are not intended to limit the scope of the invention as defined in the appended claims.

---

The embodiment of the invention in which an exclusive property or privilege is claimed is defined as follows:

1. A method for enriching specific genetic sequences, comprising:

a) immobilizing a first set of oligonucleotide molecules at a plurality of positions on a first gel substrate, said first set of oligonucleotide molecules synthesized to complement base sequences of the genetic sequences;

b) contacting genetic material with said first set of oligonucleotides, said genetic material containing the specific genetic sequences, so as to allow formation of first duplexes of said first set of oligonucleotides and fragments of the specific genetic sequences;

c) simultaneously isolating the fragments of the specific genetic material sequences from the duplexes formed via diffusion;

d) labeling the now-isolated fragments with a fluorochrome;

e) simultaneously contacting each now-labeled fragment with a second separate set of sequencing oligonucleotide molecules contained on a sequencing gel substrate, said sequencing set of oligonucleotide molecules which are complementary to subsequence regions of each now-labelled fragment, so as to allow for second duplexes to form between the subsequence regions and said sequencing set of oligonucleotide molecules; and f) isolating the subsequence regions, thereby enriching the specific genetic sequences.

2. The method as recited in claim 1 wherein the genetic material is selected from the group consisting of deoxyribonucleic acid and ribonucleic acid.

3. The method as recited in claim 1 wherein the first set and second set of oligonucleotide molecules contain bases selected from the group consisting of guanine, cytosine, adenine, thymine and uracil.

4. The method as recited in claim 1 wherein the first set of oligonucleotide molecules consist of different base sequences and are of equal length.

5. The method as recited in claim 1 wherein the oligonucleotide molecules range in length from approximately 6 and 12 bases.

6. The method as recited in claim 1 wherein the fluorochrome is selected from the group consisting of tetramethylrodamine, fluoresceine, Texas Red, Cascade Blue, Rhodamine, HEX, and combinations thereof.

7. The method as recited in claim 1 wherein the substrate is selected from the group consisting of polyacrylamide, polyamide, agarose, silicate glass matrix, and combinations thereof.

8. The method as recited in claim 1 wherein the second set of oligonucleotide molecules further comprises a universal base.

9. The method as recited in claim 8 wherein the universal base is selected from the group consisting of 5-nitroindole, 3-nitropyrrole, inosine, and combinations thereof.

10. The method as recited in claim 1 wherein said genetic material is fragmented into lengths of between approximately 250 and 30,000 bases prior to contacting said genetic material with said first set of oligonucleotides.

11. The method as recited in claim 1 wherein said now isolated fragments are fragmented into lengths of between approximately 10 to 50 bases prior to contacting said now-isolated fragments with the second set of oligonucleotides.

12. A method for enriching specific genetic sequences contained in genetic material, comprising:

a) fractionating genetic material to lengths of between approximately 250 and 30,000 bases;

b) labeling the now fractionated genetic material with a fluorochrome;

c) immobilizing a first set of oligonucleotide molecules at a plurality of positions on a first porous substrate, said first set of oligonucleotide molecules synthesized to complement base sequences of the genetic material;

d) contacting the now-labeled genetic material with said first set of oligonucleotides so as to allow formation of duplexes of said first set of oligonucleotides and the specific genetic sequences;

e) simultaneously isolating each of the specific genetic material sequences from the duplexes formed via diffusion;

f) fragmenting the now-isolated specific genetic material sequences into lengths of between approximately 10 and 50 bases;

g) labeling the now-isolated specific genetic material with a fluorochrome;

h) simultaneously contacting each now-labeled fragment with a separate set of sequencing oligonucleotide molecules contained on a sequencing gel substrate, said sequencing set of oligonucleotide molecules which are complementary to subsequence regions of each now-labelled fragment, so as to allow for second duplexes to form between the subsequence regions and said sequencing set of oligonucleotide molecules; and i) isolating the subsequence regions thereby enriching the specific genetic sequences.

13. The method as recited in claim 12 wherein the genetic material is selected from the group consisting of deoxyribonucleic acid and ribonucleic acid.

14. The method as recited in claim 12 wherein the first and second set of oligonucleotide molecules contain bases selected from the group consisting of guanine, cytosine, adenine, thymine and uracil.

15. The method as recited in claim 12 wherein the first set of oligonucleotide molecules consist of different base sequences and are of equal length.

16. The method as recited in claim 12 wherein the length of the oligonucleotides is between 6 and 12 bases.

17. The method as recited in claim 12 wherein the genetic material is labeled with a fluorochrome selected from the group consisting of tetramethylrodamine, fluoresceine, Texas Red, Cascade Blue, Rhodamine, HEX, and combinations thereof.

18. The method as recited in claim 12 wherein the substrate is selected from the group consisting of polyacrylamide gel, polyamide gel, agarose, silicate glass matrix and combinations thereof.

19. The method as recited in claim 12 wherein the second set of oligonucleotides are further comprised of a universal base.

* * * * *

SEQUENCE LISTING ( 1 ) GENERAL INFORMATION:

( i i i ) NUMBER OF SEQUENCES: 30

( 2 ) INFORMATION FOR SEQ ID NO: 1:

( i ) SEQUENCE CHARACTERISTICS:
        ( A ) LENGTH: 22 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: Primer #12005
        ( B ) LOCATION: 1-22
        ( C ) IDENTIFICATION METHOD: Primer of exons to β-thalassemia gene.
        ( D ) OTHER INFORMATION: None ( x i ) SEQUENCE DESCRIPTION: SEQ ID NO: 1:

| | |
|---|---|
| TGCCAGAAGA    GCCAAGGACA    GG | 22 |

( 2 ) INFORMATION FOR SEQ ID NO: 2:

( i ) SEQUENCE CHARACTERISTICS:
        ( A ) LENGTH: 20 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: Primer #12406
        ( B ) LOCATION: 1-20
        ( C ) IDENTIFICATION METHOD: Primer of exons to β-thalassemia
            gene.
        ( D ) OTHER INFORMATION: None.

( x i ) SEQUENCE DESCRIPTION: SEQ ID NO: 2:

| | |
|---|---|
| TAAGGGTGGG    AAAATAGACC | 20 |

( 2 ) INFORMATION FOR SEQ ID NO: 3:

( i ) SEQUENCE CHARACTERISTICS:
        ( A ) LENGTH: 20 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: Primer #12156
        ( B ) LOCATION: 1-20
        ( C ) IDENTIFICATION METHOD: Similarity with known sequences.
        ( D ) OTHER INFORMATION: Primer of exons to β-thalassemia
            gene.

( x i ) SEQUENCE DESCRIPTION: SEQ ID NO: 3:

| | |
|---|---|
| CATTTGCTTC    TGACACAACT | 20 |

( 2 ) INFORMATION FOR SEQ ID NO: 4:

( i ) SEQUENCE CHARACTERISTICS:
        ( A ) LENGTH: 19 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: Primer #12313
        ( B ) LOCATION: 1-19
        ( C ) IDENTIFICATION METHOD: Similarity with known sequences.
        ( D ) OTHER INFORMATION: Primer of exons to β-thalassemia
            gene.

( x i ) SEQUENCE DESCRIPTION: SEQ ID NO: 4:

| | |
|---|---|
| TCTCCTTAAA    CCTGTCTTG | 19 |

( 2 ) INFORMATION FOR SEQ ID NO: 5:

( i ) SEQUENCE CHARACTERISTICS:
        ( A ) LENGTH: 10 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:

(A) NAME/KEY: Primer #12272
                (B) LOCATION: 1-10
                (C) IDENTIFICATION METHOD: Similarity with known sequences.
                (D) OTHER INFORMATION: Nested primer of exons to β-
                    thalassemia gene.

(xi) SEQUENCE DESCRIPTION: SEQ ID NO: 5:

CCCTGGGCAG 10

(2) INFORMATION FOR SEQ ID NO: 6:

(i) SEQUENCE CHARACTERISTICS:
                (A) LENGTH: 14 bases
                (B) TYPE: nucleic acid
                (C) STRANDEDNESS: Not Applicable
                (D) TOPOLOGY: linear (ii) MOLECULE TYPE: Genomic DNA (ix) FEATURE:
                (A) NAME/KEY: Primer #12299
                (B) LOCATION: 1-14
                (C) IDENTIFICATION METHOD: Similarity with known sequences.
                (D) OTHER INFORMATION: Nested primer of exons to β-
                    thalassemia gene.

(xi) SEQUENCE DESCRIPTION: SEQ ID NO: 6:

GTCTTGTAAC CTTG 14

(2) INFORMATION FOR SEQ ID NO: 7:

(i) SEQUENCE CHARACTERISTICS:
                (A) LENGTH: 21 bases
                (B) TYPE: nucleic acid
                (C) STRANDEDNESS: Not Applicable
                (D) TOPOLOGY: linear (ii) MOLECULE TYPE: Genomic DNA (ix) FEATURE:
                (A) NAME/KEY: None
                (B) LOCATION: 1-21
                (C) IDENTIFICATION METHOD: Similarity with known sequences.
                (D) OTHER INFORMATION: Nested primer of exons to β-
                    thalassemia gene.

(xi) SEQUENCE DESCRIPTION: SEQ ID NO: 7:

CACTTAGACC TCACCCTAGT G 21

(2) INFORMATION FOR SEQ ID NO: 8:

(i) SEQUENCE CHARACTERISTICS:
                (A) LENGTH: 20 bases
                (B) TYPE: nucleic acid
                (C) STRANDEDNESS: Not Applicable
                (D) TOPOLOGY: linear (ii) MOLECULE TYPE: Genomic DNA (ix) FEATURE:
                (A) NAME/KEY: None
                (B) LOCATION: 1-20
                (C) IDENTIFICATION METHOD: Similarity with known sequences.
                (D) OTHER INFORMATION: Nested primer of exons to β-
                    thalassemia gene.

(xi) SEQUENCE DESCRIPTION: SEQ ID NO: 8:

GACTTTTATG CCCAGCCCTG 20

(2) INFORMATION FOR SEQ ID NO: 9:

(i) SEQUENCE CHARACTERISTICS:

( A ) LENGTH: 20 bases
( B ) TYPE: nucleic acid
( C ) STRANDEDNESS: Not Applicable
( D ) TOPOLOGY: linear ( i i ) MOLECULE TYPE: Genomic DNA ( i x ) FEATURE:
( A ) NAME/KEY: None
( B ) LOCATION: 1-20
( C ) IDENTIFICATION METHOD: Similarity with known sequences.
( D ) OTHER INFORMATION: Nested primer of exons to β-thalassemia gene.

( x i ) SEQUENCE DESCRIPTION: SEQ ID NO: 9:

GAGAAGTCTG CCGTTACTGC 20

( 2 ) INFORMATION FOR SEQ ID NO: 10:

( i ) SEQUENCE CHARACTERISTICS:
( A ) LENGTH: 20 bases
( B ) TYPE: nucleic acid
( C ) STRANDEDNESS: Not Applicable
( D ) TOPOLOGY: linear ( i i ) MOLECULE TYPE: Genomic DNA ( i x ) FEATURE:
( A ) NAME/KEY: None
( B ) LOCATION: 1-20
( C ) IDENTIFICATION METHOD: Similarity with known sequences.
( D ) OTHER INFORMATION: Nested primer of exons to β-thalassemia gene.

( x i ) SEQUENCE DESCRIPTION: SEQ ID NO: 10:

ACCTTGATAC CAACCTGCCC 20

( 2 ) INFORMATION FOR SEQ ID NO: 11:

( i ) SEQUENCE CHARACTERISTICS:
( A ) LENGTH: 21 bases
( B ) TYPE: nucleic acid
( C ) STRANDEDNESS: Not Applicable
( D ) TOPOLOGY: linear ( i i ) MOLECULE TYPE: Genomic DNA ( i x ) FEATURE:
( A ) NAME/KEY: None
( B ) LOCATION: 1-21
( C ) IDENTIFICATION METHOD: Similarity with known sequences.
( D ) OTHER INFORMATION: Nested primer of exons to β-thalassemia gene.

( x i ) SEQUENCE DESCRIPTION: SEQ ID NO: 11:

GTGGAGACAG AGAAGACTCT T 21

( 2 ) INFORMATION FOR SEQ ID NO: 12:

( i ) SEQUENCE CHARACTERISTICS:
( A ) LENGTH: 20 bases
( B ) TYPE: nucleic acid
( C ) STRANDEDNESS: Not Applicable
( D ) TOPOLOGY: linear ( i i ) MOLECULE TYPE: Genomic DNA ( i x ) FEATURE:
( A ) NAME/KEY: None
( B ) LOCATION: 1-20
( C ) IDENTIFICATION METHOD: Similarity with known sequences.
( D ) OTHER INFORMATION: Nested primer of exons to β-thalassemia gene.

( x i ) SEQUENCE DESCRIPTION: SEQ ID NO: 12:

TAGACCATAG GCAGAGAGAG                                                                                          20

( 2 ) INFORMATION FOR SEQ ID NO: 13:

( i ) SEQUENCE CHARACTERISTICS:
        ( A ) LENGTH: 8 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: None
        ( B ) LOCATION: 1-8
        ( C ) IDENTIFICATION METHOD: Similarity with known sequences.
        ( D ) OTHER INFORMATION: Complementarity with primer of
            exons to β- thalassemia gene.

( x i ) SEQUENCE DESCRIPTION: SEQ ID NO: 13:

GATTGGCC                                                                                                        8

( 2 ) INFORMATION FOR SEQ ID NO: 14:

( i ) SEQUENCE CHARACTERISTICS:
        ( A ) LENGTH: 8 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: None
        ( B ) LOCATION: 1-8
        ( C ) IDENTIFICATION METHOD: Similarity with known sequences.
        ( D ) OTHER INFORMATION: Complementarity with primer of
            exons to β- thalassemia gene.

( x i ) SEQUENCE DESCRIPTION: SEQ ID NO: 14:

CTGGGAGT                                                                                                        8

( 2 ) INFORMATION FOR SEQ ID NO: 15:

( i ) SEQUENCE CHARACTERISTICS:
        ( A ) LENGTH: 8 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: None
        ( B ) LOCATION: 1-8
        ( C ) IDENTIFICATION METHOD: Similarity with known sequences.
        ( D ) OTHER INFORMATION: Complementarity with primer of
            exons to β- thalassemia gene.

( x i ) SEQUENCE DESCRIPTION: SEQ ID NO: 15:

TCCCTGCT                                                                                                        8

( 2 ) INFORMATION FOR SEQ ID NO: 16:

( i ) SEQUENCE CHARACTERISTICS:
        ( A ) LENGTH: 8 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
    ( A ) NAME/KEY: None
    ( B ) LOCATION: 1-8
    ( C ) IDENTIFICATION METHOD: Similarity with known sequences.
    ( D ) OTHER INFORMATION: Complementarity with primer of
        exons to β- thalassemia gene.

( x i ) SEQUENCE DESCRIPTION: SEQ ID NO: 16:

T T G C C C C A        8

( 2 ) INFORMATION FOR SEQ ID NO: 17:

( i ) SEQUENCE CHARACTERISTICS:
    ( A ) LENGTH: 8 bases
    ( B ) TYPE: nucleic acid
    ( C ) STRANDEDNESS: Not Applicable
    ( D ) TOPOLOGY: linear ( i i ) MOLECULE TYPE: Genomic DNA ( i x ) FEATURE:
    ( A ) NAME/KEY: None
    ( B ) LOCATION: 1-8
    ( C ) IDENTIFICATION METHOD: Similarity with known sequences.
    ( D ) OTHER INFORMATION: Complementarity with primer of
        exons to β- thalassemia gene.

( x i ) SEQUENCE DESCRIPTION: SEQ ID NO: 17:

C G T T C A C C        8

( 2 ) INFORMATION FOR SEQ ID NO: 18:

( i ) SEQUENCE CHARACTERISTICS:
    ( A ) LENGTH: 8 bases
    ( B ) TYPE: nucleic acid
    ( C ) STRANDEDNESS: Not Applicable
    ( D ) TOPOLOGY: linear ( i i ) MOLECULE TYPE: Genomic DNA ( i x ) FEATURE:
    ( A ) NAME/KEY: None
    ( B ) LOCATION: 1-8
    ( C ) IDENTIFICATION METHOD: Similarity with known sequences.
    ( D ) OTHER INFORMATION: Complementarity with primer of
        exons to β- thalassemia gene.

( x i ) SEQUENCE DESCRIPTION: SEQ ID NO: 18:

C C A C C A C T        8

( 2 ) INFORMATION FOR SEQ ID NO: 19:

( i ) SEQUENCE CHARACTERISTICS:
    ( A ) LENGTH: 8 bases
    ( B ) TYPE: nucleic acid
    ( C ) STRANDEDNESS: Not Applicable
    ( D ) TOPOLOGY: linear ( i i ) MOLECULE TYPE: Genomic DNA ( i x ) FEATURE:
    ( A ) NAME/KEY: None
    ( B ) LOCATION: 1-8
    ( C ) IDENTIFICATION METHOD: Similarity with known sequences.
    ( D ) OTHER INFORMATION: Complementarity with primer of
        exons to β- thalassemia gene.

( x i ) SEQUENCE DESCRIPTION: SEQ ID NO: 19:

C C C A A G A G        8

( 2 ) INFORMATION FOR SEQ ID NO: 20:

( i ) SEQUENCE CHARACTERISTICS:
   ( A ) LENGTH: 8 bases
   ( B ) TYPE: nucleic acid
   ( C ) STRANDEDNESS: Not Applicable
   ( D ) TOPOLOGY: linear ( i i ) MOLECULE TYPE: Genomic DNA ( i x ) FEATURE:
   ( A ) NAME/KEY: None
   ( B ) LOCATION: 1-8
   ( C ) IDENTIFICATION METHOD: Similarity with known sequences.
   ( D ) OTHER INFORMATION: Complementarity with primer of
        exons to β- thalassemia gene.

( x i ) SEQUENCE DESCRIPTION: SEQ ID NO: 20:

C C T A T C A G                                                                                      8

( 2 ) INFORMATION FOR SEQ ID NO: 21:

( i ) SEQUENCE CHARACTERISTICS:
      ( A ) LENGTH: 8 bases
      ( B ) TYPE: nucleic acid
      ( C ) STRANDEDNESS: Not Applicable
      ( D ) TOPOLOGY: linear ( i i ) MOLECULE TYPE: Genomic DNA ( i x ) FEATURE:
      ( A ) NAME/KEY: None
      ( B ) LOCATION: 1-8
      ( C ) IDENTIFICATION METHOD: Similarity with known sequences.
      ( D ) OTHER INFORMATION: Complementarity with primer of
           exons to β- thalassemia gene.

( x i ) SEQUENCE DESCRIPTION: SEQ ID NO: 21:

G T C A G T G C                                                                                      8

( 2 ) INFORMATION FOR SEQ ID NO: 22:

( i ) SEQUENCE CHARACTERISTICS:
      ( A ) LENGTH: 10 bases
      ( B ) TYPE: nucleic acid
      ( C ) STRANDEDNESS: Not Applicable
      ( D ) TOPOLOGY: linear ( i i ) MOLECULE TYPE: Genomic DNA ( i x ) FEATURE:
      ( A ) NAME/KEY: Normal
      ( B ) LOCATION: 1-10
      ( C ) IDENTIFICATION METHOD: Similarity with known sequences.
      ( D ) OTHER INFORMATION: Complementarity with primer of
           exons to β- thalassemia gene.

( x i ) SEQUENCE DESCRIPTION: SEQ ID NO: 22:

T C C A A C C A T A                                                                                 1 0

( 2 ) INFORMATION FOR SEQ ID NO: 23:

( i ) SEQUENCE CHARACTERISTICS:
      ( A ) LENGTH: 10 bases
      ( B ) TYPE: nucleic acid
      ( C ) STRANDEDNESS: Not Applicable
      ( D ) TOPOLOGY: linear ( i i ) MOLECULE TYPE: Genomic DNA ( i x ) FEATURE:
      ( A ) NAME/KEY: IVS I/1
      ( B ) LOCATION: 1-10
      ( C ) IDENTIFICATION METHOD: Similarity with known sequences.
      ( D ) OTHER INFORMATION: Complementarity with primer of exons to β- thalassemia gene.

( x i ) SEQUENCE DESCRIPTION: SEQ ID NO: 23:

T C T A A C C A T A                                                                                                                                  1 0

( 2 ) INFORMATION FOR SEQ ID NO: 24:

( i ) SEQUENCE CHARACTERISTICS:
        ( A ) LENGTH: 10 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: IVS I/5
        ( B ) LOCATION: 1-10
        ( C ) IDENTIFICATION METHOD: Similarity with known sequences.
        ( D ) OTHER INFORMATION: Complementarity with primer of
            exons to β- thalassemia gene.

( x i ) SEQUENCE DESCRIPTION: SEQ ID NO: 24:

T C C A A C G A T A                                                                                                                                  1 0

( 2 ) INFORMATION FOR SEQ ID NO: 25:

( i ) SEQUENCE CHARACTERISTICS:
        ( A ) LENGTH: 10 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: IVS I/6
        ( B ) LOCATION: 1-10
        ( C ) IDENTIFICATION METHOD: Similarity with known sequences.
        ( D ) OTHER INFORMATION: Complementarity with primer of
            exons to β- thalassemia gene.

( x i ) SEQUENCE DESCRIPTION: SEQ ID NO: 25:

T C C A A C C G T A                                                                                                                                  1 0

( 2 ) INFORMATION FOR SEQ ID NO: 26:

( i ) SEQUENCE CHARACTERISTICS:
        ( A ) LENGTH: 10 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: C26+
        ( B ) LOCATION: 1-10
        ( C ) IDENTIFICATION METHOD: Similarity with known sequences.
        ( D ) OTHER INFORMATION: Complementarity with primer of
            exons to β- thalassemia gene.

( x i ) SEQUENCE DESCRIPTION: SEQ ID NO: 26:

A C C A C T C C G G                                                                                                                                  1 0

( 2 ) INFORMATION FOR SEQ ID NO: 27:

( i ) SEQUENCE CHARACTERISTICS:
        ( A ) LENGTH: 10 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
    ( A ) NAME/KEY: C26-
    ( B ) LOCATION: 1-10
    ( C ) IDENTIFICATION METHOD: Similarity with known sequences.
    ( D ) OTHER INFORMATION: Complementarity with primer of
        exons to β- thalassemia gene.

( x i ) SEQUENCE DESCRIPTION: SEQ ID NO: 27:

ACCATTCCGG       10

( 2 ) INFORMATION FOR SEQ ID NO: 28:

( i ) SEQUENCE CHARACTERISTICS:
        ( A ) LENGTH: 26 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: Fragmented PCR Product
        ( B ) LOCATION: 1-26
        ( C ) IDENTIFICATION METHOD: Similarity with known sequences.
        ( D ) OTHER INFORMATION: None ( x i ) SEQUENCE DESCRIPTION: SEQ ID NO: 28:

TGGTGAGGCC CTGGGCAGGT TGGTAT       26

( 2 ) INFORMATION FOR SEQ ID NO: 29:

( i ) SEQUENCE CHARACTERISTICS:
        ( A ) LENGTH: 19 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: Fragmented PCR Product
        ( B ) LOCATION: 1-19
        ( C ) IDENTIFICATION METHOD: Similarity with known sequences.
        ( D ) OTHER INFORMATION: None ( x i ) SEQUENCE DESCRIPTION: SEQ ID NO: 29:

CCTGGGCAGN TTGGNATCA       19

( 2 ) INFORMATION FOR SEQ ID NO: 30:

( i ) SEQUENCE CHARACTERISTICS:
        ( A ) LENGTH: 8 bases
        ( B ) TYPE: nucleic acid
        ( C ) STRANDEDNESS: Not Applicable
        ( D ) TOPOLOGY: linear ( i i ) MOLECULE TYPE: Genomic DNA ( i x ) FEATURE:
        ( A ) NAME/KEY: Fragmented PCR Product
        ( B ) LOCATION: 1-8
        ( C ) IDENTIFICATION METHOD: Similarity with known sequences.
        ( D ) OTHER INFORMATION: None ( x i ) SEQUENCE DESCRIPTION: SEQ ID NO: 30:

CNAACCNT       8